United States Patent [19]

Johnson

[11] Patent Number: 5,753,105
[45] Date of Patent: May 19, 1998

[54] AUTOMATIC FILTRATION AND EXTRACTION DEVICE AND METHOD

[76] Inventor: Robert S. Johnson, 25 Blue Heron Ave., Hampstead, N.H. 03841

[21] Appl. No.: 522,237

[22] PCT Filed: Mar. 1, 1994

[86] PCT No.: PCT/US94/02163

§ 371 Date: Nov. 5, 1995

§ 102(e) Date: Nov. 5, 1995

[87] PCT Pub. No.: WO94/20379

PCT Pub. Date: Sep. 15, 1994

Related U.S. Application Data

[63] Continuation-in-part of Ser. No. 025,663, Mar. 3, 1993, abandoned.

[51] Int. Cl.$^6$ .............................. B01D 17/12; B01D 11/00
[52] U.S. Cl. .................... 210/86; 210/141; 210/406; 210/511; 422/68.1; 422/101; 422/103
[58] Field of Search .................. 422/62, 63, 67, 422/101, 102, 103, 106, 69, 104, 68.1; 436/49, 177, 178; 73/863.01, 863.02, 863.23, 863.24, 863.25; 96/4; 55/270; 210/86, 97, 110, 141, 143, 205, 348, 511, 634, 636, 138, 139, 140, 232, 406, 416.1, 455, 456, 498

[56] References Cited

U.S. PATENT DOCUMENTS

| | | | |
|---|---|---|---|
| 2,091,810 | 8/1937 | Ferraez, Jr. | 73/863.23 |
| 4,247,399 | 1/1981 | Pitesky | 210/406 |
| 4,598,049 | 7/1986 | Zelinka et al. | 422/62 |
| 4,649,028 | 3/1987 | Kaltenbach et al. | 422/63 |
| 4,701,304 | 10/1987 | Horn et al. | 422/62 |
| 4,783,318 | 11/1988 | Lapakko | 210/406 |
| 4,835,707 | 5/1989 | Amano et al. | 73/863.25 |
| 4,890,484 | 1/1990 | Telfer et al. | |
| 5,240,680 | 8/1993 | Zuckermann et al. | 422/67 |

FOREIGN PATENT DOCUMENTS

| | | |
|---|---|---|
| 3922333 A1 | 1/1991 | Germany. |
| 4112239 C1 | 7/1992 | Germany. |

*Primary Examiner*—Joseph W. Drodge
*Attorney, Agent, or Firm*—Hamilton, Brook, Smith & Reynolds, P.C.

[57] ABSTRACT

An improved automatic filtration and extraction device is disclosed which comprises a base 17 defining at a top end a broadened cavity area which tapers downwardly and inwardly from the top end to define a chamber for a portion and then defines a plurality of effluent outlets at the bottom end each extending from the chamber to an outer surface of the body. Sealers 42 are adapted to each of the effluent outlets and are moveable between a first closed position sealing the effluent outlet and a second open position to allow the passage of effluent through the effluent outlet. A filter 110 is detachably and removeably adapted over the broadened cavity area. A solvent provider 90 is adapted to the base whereby various solvents are provided to the broadened cavity area. A circuit 200 is connected at one end to a power source, and the programmable memory to access and direct the sequence of events after an initial event. A programmable memory is provided for a sequence of events and is connected to the base. A vacuum is adapted to each of the effluent outlets each having an "ON" position whereby a vacuum is provided to induce effluent flow through the effluent outlet and to seal all other outlets, and an "OFF" position eliminating vacuum to that effluent outlet.

15 Claims, 5 Drawing Sheets

AUTOMATIC FILTRATION AND EXTRACTION DEVICE AND METHOD

RELATED APPLICATIONS

This is a Continuation-In-Part of application Ser. No. 08/025,663, filed Mar. 3, 1993, abandoned which is incorporated herein by reference in its entirety.

BACKGROUND OF THE INVENTION

Increasing interest, including concern for the environment has lead to more and more quality control of air and water.

Analytical methods used by laboratories to analyze aqueous samples for organic components, require laboratory personnel to follow very specific and time consuming operations. As more samples need to be analyzed, laboratories are looking for new ways to handle the increased sample load, and at the same time, to provide accurate and reproducible data.

To aid in this endeavor, recent methodology improvements by the US EPA have introduced a filtration procedure, whereby organics are chemically removed from the water sample. The water sample is passed through a filter media which contains a chemical adsorbent. Once the water sample has passed through the filter, the filter is extracted with an organic solvent. This solvent is collected and later analyzed.

A number of problems are associated with this filtration procedure. First, in order to ensure the filter media is properly conditioned, the filter must be washed and soaked with organic solvents, in a proper sequence, in order to change the polarity of the filter media. As the filter media is being conditioned, it is critical that the surface of the filter media not be exposed to air. Once the water sample has been filtered, the filter media must be carefully soaked and eluted to ensure adequate recovery of the organics of interest. These time critical, and time consuming steps, make consistent and reproducible recoveries difficult to achieve.

There exists a great need for precise automated devices and methods for sample analysis.

SUMMARY OF THE INVENTION

I have discovered an improved automatic filtration and extraction device which comprises a base means defining at a top end thereof a substantially broadened cavity area, tapering downwardly and inwardly from said top end thereof to further define a chamber means for a portion thereof and then further defining a plurality of effluent outlet means at a bottom end thereof, each extending from said chamber means to an outer surface of said body means. A plurality of sealing means are adapted to each of said outlet means. Each is moveable between a first closed position sealing said outlet means and a second open position allowing the passage of effluent. A filter means detachably and removeably adapts over said substantially broadened cavity area. Solvent providing means are adapted to said housing means whereby various solvents are provided to said substantially broadened cavity area. Programmable memory means are connected to the housing means and provide a series of events. Circuit means are connected to a power source and to the programmable memory means to access and direct a sequence of events after an initial event. Vacuum means are adapted to each of said effluent outlet means, each vacuum means having an "ON" position whereby vacuum is provided to induce effluent flow through said effluent outlet means and to seal off the other effluent outlet means, preventing "backflow", and an "OFF" position eliminating vacuum.

My method for improved automatic filtration and extraction comprises the steps of placing a filter, specifically designed for a specific adsorbate, in the extraction device. The filter is then washed with a cleansing solvent. The sample is then filtered with the desired chemicals adsorbed in the filter. The test simple is then extracted from the filter by a preferred solvent and deposited in a sample tube.

Preferably but optionally my improved automatic filtration and extraction device includes a directed flow solvent dispensing ring so that the introduction of solvent may be made in as uniform a manner as possible to thoroughly wash down the internal walls of my device.

Preferably but optionally the filter means in my improved extraction device includes a filter of the type in which a desired adsorbate is specifically adsorbed and then extracted. More particularly, these filters such as 3M's EMPORE® filter can be made for specific adsorption of various organics in drinking water.

Preferably, but optionally, all the active surfaces, including the balls in the outlet sealing means, of my improved automatic filtration and extraction device are made from an inert material, more particularly a thermoplastic, and particularly a chlorinated fluorocarbon polymer, particularly Teflon®.

Preferably, but optionally, my improved extraction device includes a fluid sample sensor so that as the sample is introduced there is always sufficient sample to keep the filter wet. In the preferred embodiment a pair of thermistors are placed one above the other to maintain a predetermined level.

Preferably my "chamber means" is made as small as practicable to keep "dead volume" in the chamber to a minimum so that as little cross-contamination as possible will occur. All aspects of the chamber are scrutinized scrupulously to minimize any cross-contamination or "back flow" contamination. Various materials including ruby and sapphire have been studied, and Teflon was selected.

Preferably, but optionally, the end of each effluent outlet means adjacent the "chamber means" has an annular collar in which the ball of the sealing mechanism seats to maximize sealing of that effluent outlet means.

My invention provides numerous advantages over those devices found in the prior art.

It is an advantage of my improved automatic extraction and filtration device that samples can be processed rapidly and yet very accurately. The device provides for directed liquid flow of any solvent introduction, therefore making each extraction more uniform.

My invention also provides minimization of cross contaminatability by solvents and extraction products.

Other advantages of my improved extraction device are that it is strong and durable, simple to manufacture, efficient and economical.

These and other advantages of my invention will become apparent when viewed in light of the accompanying drawings and following detailed description.

DETAILED DESCRIPTION OF DRAWINGS

Figure 1:
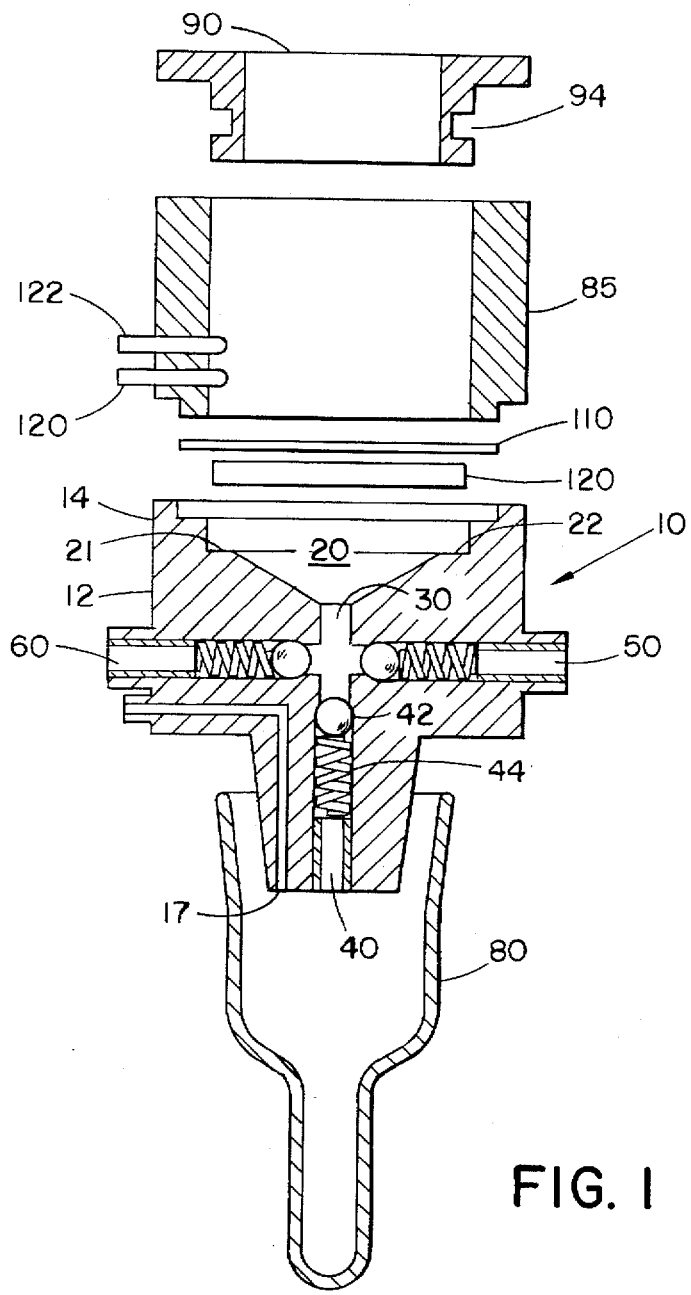
FIG. 1 is a cut-away front view of my improved automatic filtration and extraction device.

Referring now in particular to the accompanying drawings, my improved automatic filtration and extraction device is generally indicated at 10 in FIG. 1 and includes base 12. Broadened cavity area 20 tapers downwardly to chamber 30 which extends downwardly to effluent outlets 40, 50, 60 each of which has a ball closure 42 and retaining ball seat and spring 44 (52, 54, 62, 64 respectively). Effluent outlet 40 extends to the end of the base 12. Detachable collector vessel. 80 adapts around the end of base 12. Vent 17 decants the vacuum from the detachable collection vessel.

Figure 2:
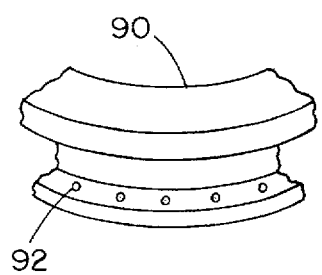
FIG. 2 is an isometric view of a segment of the solvent dispensing ring of FIG. 1.

Collar 85 fits into the base and contains thermistors 120, 122 the ends of which extend out onto the cavity area. Directed flow solvent dispensing ring 90 (FIG. 2) fits over the collar 85, aligned with the periphery of the base top end 14 and includes apertures 92 (FIG. 2). Flow channel 94 extends around the directed flow solvent dispensing ring and includes a connecting passage 96 (not shown).

Solvent dispenser 100 (not shown) is connected to a series of solvent reservoirs 104 (not shown) and to the directed flow solvent dispensing ring.

FIG. 1 depicts filter 110 positioned on filter screen support 121 which fits into slots 21, 22 of broadened cavity area 20. Thermistors 120, 122 (FIG. 1) are situated in the collar 85, slightly above the filter surface to control the level of liquid. As the level of liquid rises above the first thermistor 120, it activates that thermistor and as the liquid level rises past the second thermistor 122, the liquid level activates that thermistor, so that whenever the liquid level falls below the second thermistor, more sample is provided. Vacuum (140, 150, 160 not shown) is connected to each effluent outlet 40, 50, 60 to assist withdrawal of effluent. Micro processor controls 155 (FIG. 3) actuate the solvent dispenser and thermistor control and the opening and shutting of the ball closure in each effluent outlet by opening and closing electronic solenoid valves.

Figure 3:
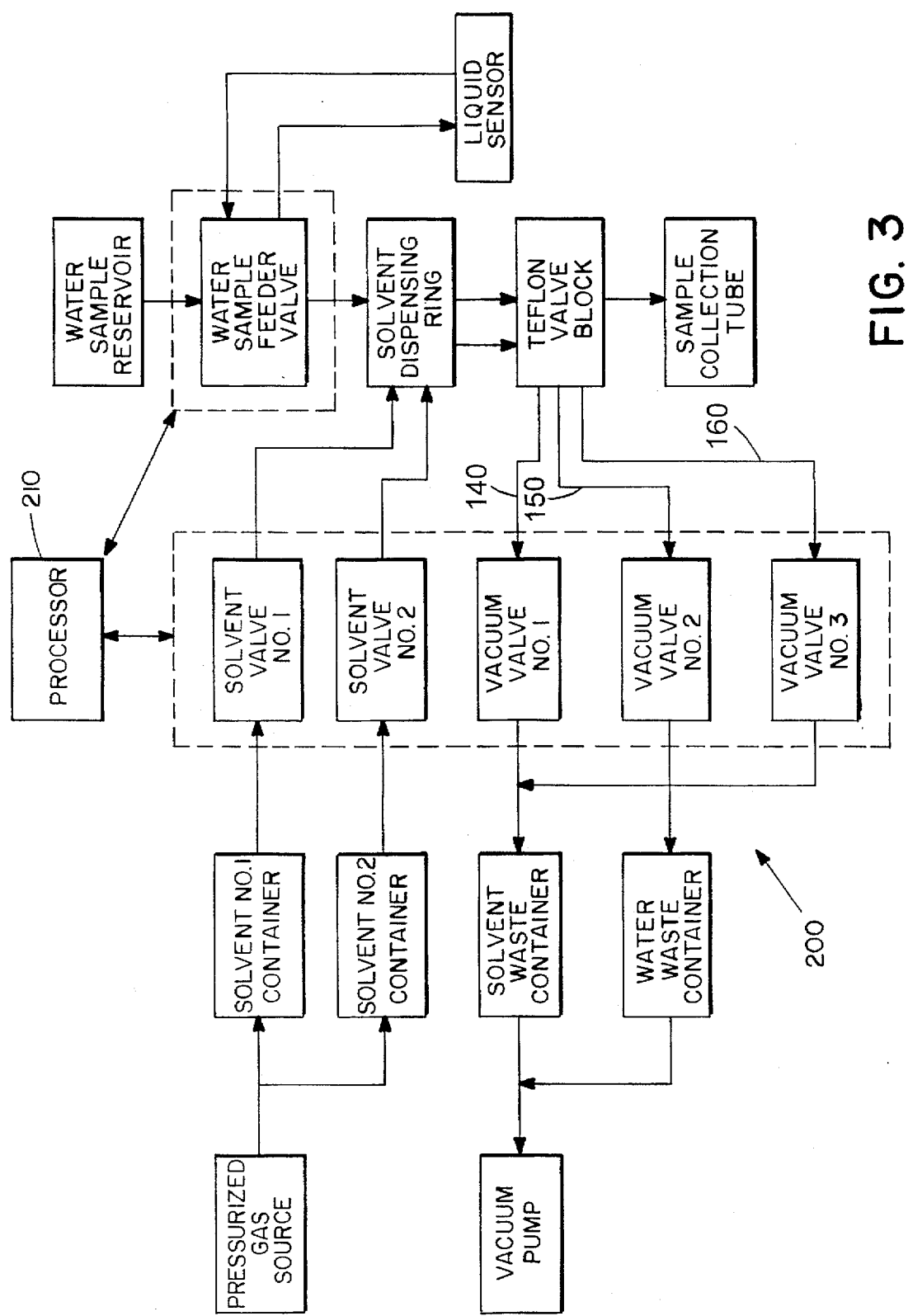
FIG. 3 is an overall schematic.

FIG. 3 details a schematic of the improved filtration and extraction device or "station" 200 which is connected to a central "controller" 210 which controls one or more "stations". The controller 210 is interfaced to each station 200 using an eight wire cable connector 220 of a type known commercially as "Telco" or similar style. There is one microprocessor for the controller and one microprocessor in each station.

The cable connector contains communication from the microprocessor in the controller to each station. It also contains the power needed to run the valves and microprocessor in the station. Each station contains a microprocessor, valves and relays to control the station. Commands are sent from the controller to each active station. These commands are processed locally by the microprocessor in each station. The microprocessor uses the command information to change the state of the valves. The controller has only a ROM external memory for firmware program storage. It uses the 128 byte internal memory of the microprocessor for all other activities. The valves in each station are controlled by a solid state relay.

Figure 4:
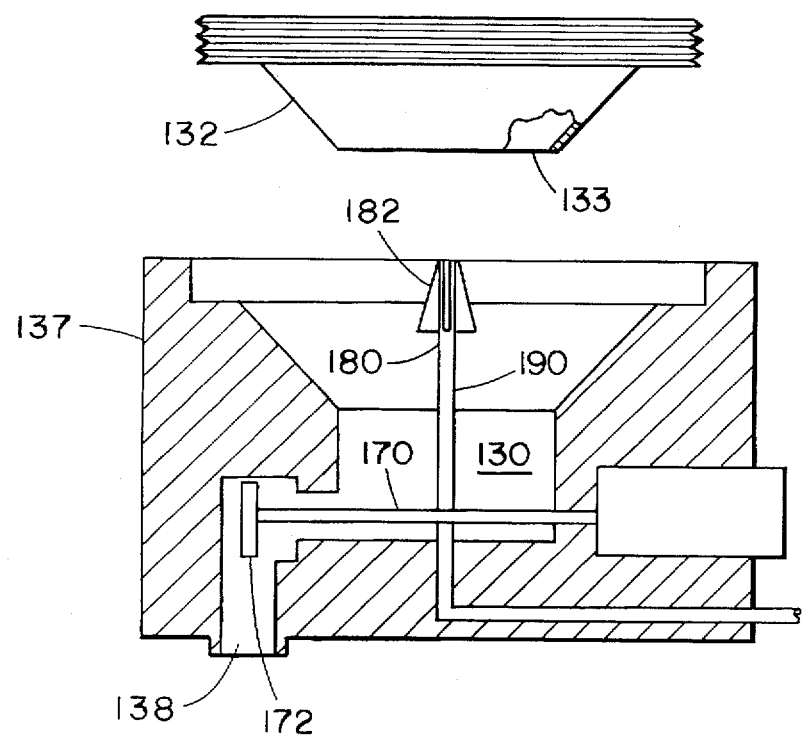
FIG. 4 is a cut-away side view of the sample dispenser and sample bottle cap.

FIG. 4 depicts reservoir 130 of my improved automatic filtration and extraction device. Water samples are collected in bottles 131 (not shown). The top of the water sample is removed. A pierceable-foil material is put in place over the top of the sample bottle and screw top 132 having opening 133 is screwed onto the top of the sample bottle. The sample bottle is inverted and put into place over the sample provider 137 and lowered onto piercing barb 180 piercing the foil material allowing the sample to flow into the sample provider. Random spray solvent washer tube 190 including spray holes 192 (not shown) in piercing barb 180 which has fins 182 Piston 170 includes a flange end 172 which closes and opens sample port 138. When directed to provide water by thermistor 122 the piston retracts from the port and water flows onto the filter.

In operation the filter is positioned on the filter screen support. The system is actuated and solvent is automatically dispensed from apertures in the directed flow solvent dispensing ring rinsing the filter and the broadened cavity area. This solvent is then evacuated through chamber 30 and effluent outlet 50 (although the embodiment can be programmed to utilize any effluent outlet).

At the end of this rinsing, effluent outlet 50 closes automatically and a test sample is dispensed onto the filter from the reservoir. When the sample bottle 131 is empty, solvent is sprayed within the sample bottle from the top of the piercing barb ensuring maximum collection of sample.

Water samples are collected in bottles which have a destructible foil closure in the top. The water bottle is inverted and the foil seal is torn by the piercing barb as the bottle cap is set into place on the top of the reservoir. The water flows into the reservoir where it is held until the higher thermistor signals that more water is required on the filter. The piston upon a signal by the thermistor opens the reservoir gate and water flows onto the filter until the thermistor signals shut off or the water sample is exhausted.

The liquid level of the sample remains sufficient to keep the filter wet.

The water sample is then filtered and the organics adsorbed onto the filter. A second effluent outlet 60 is opened and the water is evacuated through it. This second effluent outlet is then closed and the extracting solvent is introduced taking the adsorbed sample from the filter through effluent outlet 40 into the detachable collection tube. The detachable collection tube is removed, another inserted in it place and the cycle repeats.

Figure 6:
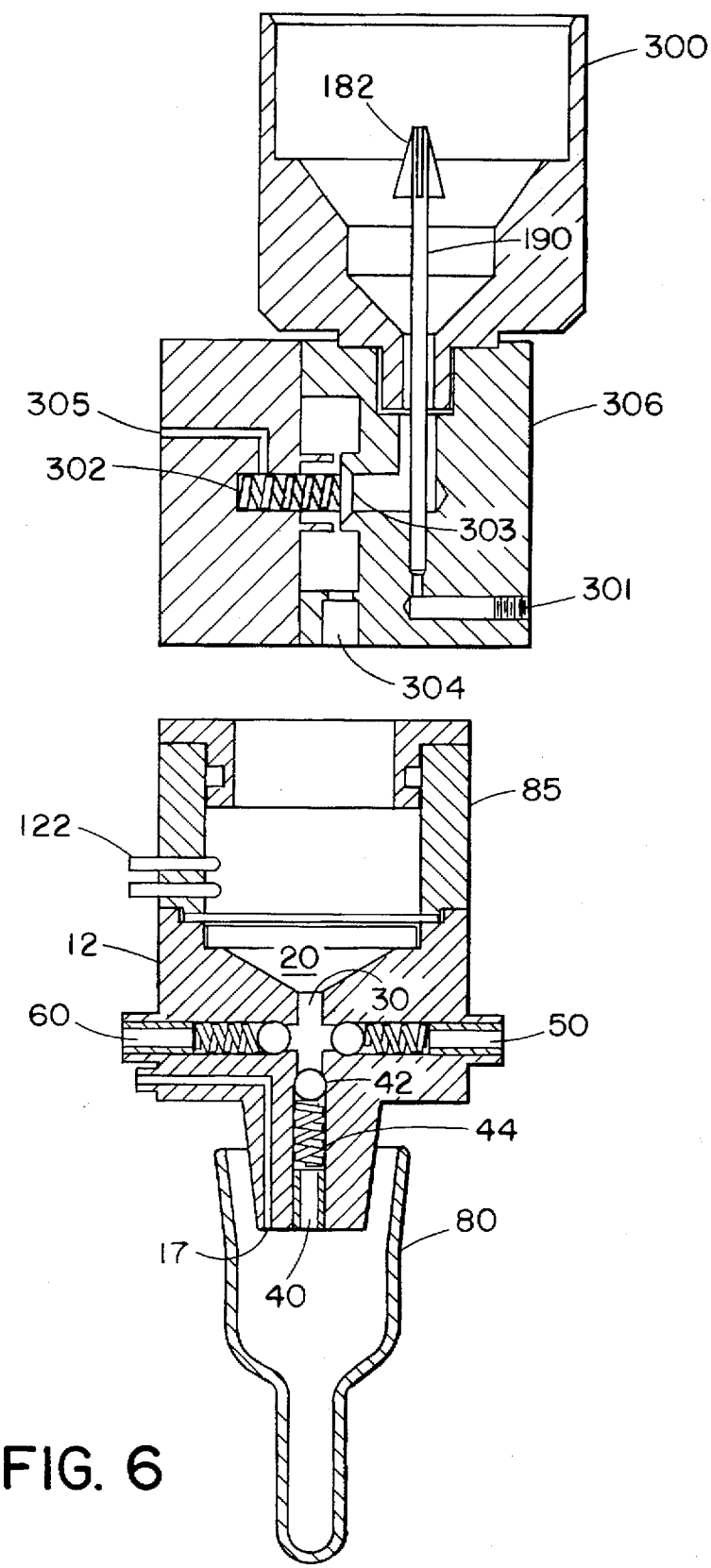
FIG. 6 is a cross-sectional view of a modified sample dispenser over the filtration and extraction device of FIG. 1.

A modified sample diagram positioned over the filtration and extraction device of FIG. 1 is shown in FIG. 6. Once the water bottle is placed into the bottle holder 300, the piercing barb 182 pierces the foil material, allowing the water sample to drain into the water valve body 306. At the proper time during the sequence, a vacuum valve opens which pulls a vacuum through the vacuum port fitting 305. The vacuum pulls against spring 302 which pulls the plunger 303 off the seat. This allows the water sample to drain down into the cavity area 20 and begin to fill up. When the water level reaches the top fluid level sensor 122 the vacuum valve closes (not shown) which allows the spring 302 to force the plunger 303 closed, stopping the water flow. The water sample is removed from the cavity area by flowing out the port.

When the water level reaches the lower fluid level sensor 120, the vacuum valve (not shown) opens, pulling the plunger 303 off the seat, allowing the water sample to drain into the disk area. When the water level reaches the top liquid sensor, the plunger closes, stopping the flow of water. This sequence is repeated until all of the water has been removed.

Figure 5:
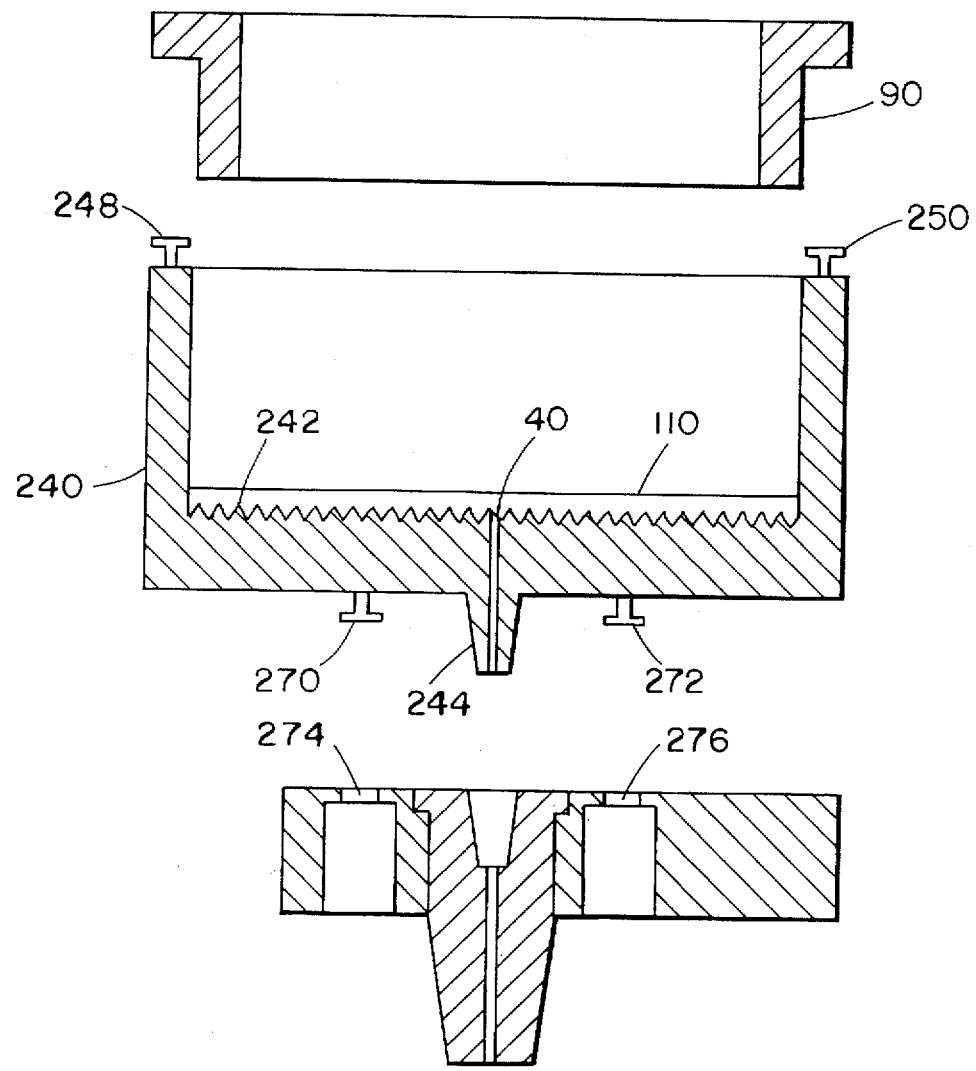
FIG. 5 is a cut away side view of an alternative embodiment of the filter module.

FIG. 5 depicts an alternative embodiment of the filter area. Filter module 240 includes saw toothed filter bed 242, cavity adapter section 244 and fastener brackets 248, 250 which retain filter ring 260 in place. Extending radially outward from the outlet 40 to the perimeter of the sawtoothed bed are collection channels 265 (not shown) to facilitate sample collection. Fastening pins 270, 272 detachably connect the filter module to corresponding fastener recesses 274, 276 on the base.

This alternative embodiment permits the filter to be changed or detached for analysis from the invention with minimal possible contamination.

Several modifications changes and adaptions can be made by those skilled in the art without departing from the scope of the invention.

Therefore, different means may be substituted by other types of design and are anticipated by this invention.

Accordingly, it is the intention of the inventor to include all such modifications which shall cone within the true scope of the invention which is defined by the appended claims.

I claim:

1. An improved automatic filtration and extraction device comprising:
   a) base means defining at a top end thereof a cavity area which defines a chamber means for a portion thereof and then further defining a plurality of effluent outlet means at a bottom end thereof each extending from said chamber means to an outer surface of said base means;
   b) sealing means adapted to each of said effluent outlet means moveable between a first closed position sealing said effluent outlet means and a second open position to allow the passage of effluent through said effluent outlet means;
   c) filter means detachably and removably adapted over said cavity area;
   d) solvent providing means adapted to said base means wherein various solvents are provided to said cavity area;
   e) vacuum means respectively adapted to each of said effluent outlet means, each vacuum means having an "ON" position whereby a vacuum is provided to induce effluent flow through said effluent outlet means and prevent flow through all other said outlet means, and an "OFF" position eliminating vacuum to that effluent outlet means; and
   f) circuit means comprising a programmable memory means including means to access and to direct a sequence of events controlling movement of solvents and effluent through said device after an initial event, said circuit means being connected to said solvent providing means and said respective vacuum means such that a specific order of activations and deactivations of said solvent providing means and each of said vacuum means are time determined and provide for a particular extraction in said device.

2. The improved automatic filtration and extraction device of claim 1 further comprising:
   sample collection means detachably and removably adapting over said bottom end of said base means.

3. The improved automatic filtration and extraction device of claim 1 further comprising:
   level sensing means arranged over said filter means by which sufficient sample is maintained during filtration.

4. The improved automatic filtration and extraction device of claim 1 wherein the solvent providing means further includes:
   solvent lip means disposed above said cavity area, defining a multiplicity of perforations therein; and
   said solvent providing means connected to one or more of said multiplicity of perforations of said solvent lip means, arranged to introduce solvent unidirectionally to said chamber means.

5. The improved automatic filtration and extraction device of claim 1 wherein said filter means further comprises:
   a filter to specifically extract a certain filtrate.

6. The improved automatic filtering and extraction device of claim 1 further comprising:
   annular collar means fixedly mounted within each of said effluent outlet means adjacent said chamber means to seat said respective sealing means when said sealing means is in said first closed position.

7. The improved automatic filtration and extraction device of claim 1 wherein said plurality of effluent outlet means further comprise:
   variable sequencing means adapted to said programmable memory means to preset an order of flow through said effluent outlet means utilized in a particular filtration and extraction.

8. The improved filtration and extraction device of claim 1 further comprising:
   sample providing means arranged above said filter means defining therein an intake port for the introduction of a sample therein and an exhaust port having an open position wherein sample flows from said exhaust port onto said filter means and a closed position wherein sample is retained in said sample providing means and further defining a reservoir between said intake port and said exhaust port; and
   means to open and close said exhaust port adapted to said sample providing means.

9. The improved filtration and extraction device of claim 8 further comprising:
   solvent wash means connected to said solvent providing means at a first end thereof and extending therefrom into said sample providing means at a second end to spray solvent into said sample providing means wherein the inside surface of said sample providing means can be washed down between samples.

10. The improved filtration and extraction device of claim 9 wherein:
    said solvent wash means includes at said second end barb means such that a sealed sample may be pierced allowing the flow of sample.

11. The improved filtration and extraction device of claim 10 further comprising:
    rounded cap means defining in the center thereof an aperture such that when said cap means is fitted over a sample bottle, said sample bottle can be inverted, placed into said sample providing means and pierced through said aperture by said barb means permitting said sample to flow into said sample providing means.

12. The improved filtration and extraction device of claim 8 wherein said sample providing means further comprises:
    piston means responsive to said programmable memory means, moveable between a first position opening said exhaust port of said sample providing means and a second position closing said exhaust port.

13. The improved filtration and extraction device of claim 1 where each said sealing means further comprises:
    sealing ball means moveable between a first sealed position closing said effluent outlet means and a second unsealed position opening said effluent outlet means; and spring means affixed to each of said sealing ball means in a first position holding said sealing ball means in said sealed position and in a second position releasing said sealed ball means to said second unsealed position.

14. An improved automatic filtration and extraction device comprising:
   a) base means defining at a top end thereof a cavity area tapering downwardly and inwardly from said top end thereof to further define a chamber means for a portion thereof and then further defining a plurality of effluent outlet means at a bottom end thereof each extending from said chamber means to an outer surface of said base means;
   b) sealing means adapted to each of said effluent outlet means moveable between a first closed position sealing said effluent outlet means and a second open position to allow the passage of effluent through said effluent outlet means, each sealing means having a sealing ball means moveable between a first sealed position closing said effluent outlet means and a second unsealed position opening said effluent outlet means and spring means affixed to each of said sealing ball means in a first position holding said sealing ball means in said sealed position and in a second position releasing said sealing ball means to said second unsealed position;
   c) filter means detachably and removably adapted over said area;
   d) solvent providing means adapted to said base means wherein various solvents are provided to said cavity area said solvent providing means including a sample, and providing means arranged above said filter means defining therein an intake port for the introduction of a sample therein and an exhaust port having an open position wherein sample flows from said exhaust port onto said filter means and a closed position wherein sample is retained in said sample providing means and further defining a reservoir between said intake port and said exhaust port and having means to open and close said exhaust port adapted to said sample providing means;
   e) vacuum means respectively adapted to each of said effluent outlet means, each vacuum means having an "ON" position whereby a vacuum is provided to induce effluent flow through said effluent outlet means and prevent flow through all other said effluent outlet means, and an "OFF" position eliminating vacuum to that effluent outlet means;
   f) circuit means comprising said programmable memory means including means to access and to direct a sequence of events controlling movement of solvents and effluent through said device after an initial event, said circuit means being connected to said solvent providing means and said respective vacuum means such that said circuit means controls said sequence of events;
   g) sample collection means detachably and removably adapting over said bottom end of said base means;
   h) level sensing means arranged over said filter means whereby sufficient sample is maintained during filtration;
   i) annular collar means fixedly mounted within each of said effluent outlet means adjacent said chamber means to seat said respective sealing means when said sealing means is in said first closed position; and
   j) solvent wash means connected to said solvent providing means at a first end thereof and extending therefrom into said sample providing means at a second end to spray solvent into said sample providing means wherein the inside surface of said sample providing means can be washed down between samples and having barb means such that a sealed sample may be pierced allowing the flow of sample.

15. An improved automatic filtration and extraction device comprising:
   base means defining at a top end thereof a cavity area which defines a chamber means for a portion thereof and further defining a plurality of effluent outlet means at a bottom end thereof, each extending from said chamber means;
   sealing means adapted to each of said effluent outlet means;
   filter means adapted over said cavity area; solvent providing means adapted to said base means;
   vacuum means respectively adapted to each of said effluent outlet means, each vacuum means having an "ON" position whereby a vacuum is provided to induce effluent flow through said effluent outlet means and prevent flow through all other said outlet means, and an "OFF" position eliminating vacuum to that effluent outlet means and circuit means for controlling movement of fluid through said device, connected to said respective vacuum means, such that a specific order of activations and deactivations of each of said vacuum means are time determined for providing flow of effluent.

* * * * *